United States Patent [19]
Brichard et al.

[11] 3,992,317
[45] Nov. 16, 1976

[54] PARTICULATE PEROXYGEN COMPOUNDS

[75] Inventors: Jean Brichard, Vilvoorde; Jean-Claude Colery, Brussels, both of Belgium

[73] Assignee: Interox, Brussels, Belgium

[22] Filed: Jan. 25, 1974

[21] Appl. No.: 436,679

[30] Foreign Application Priority Data
Jan. 29, 1973 Luxemburg............................ 66925

[52] U.S. Cl............................... 252/186; 252/95; 252/99; 423/272; 423/274; 427/221
[51] Int. Cl.$^2$....................... C11D 7/54; B01J 13/02
[58] Field of Search....................... 252/186, 95, 99; 423/272, 274, 582; 427/221

[56] References Cited
UNITED STATES PATENTS

| | | |
|---|---|---|
| 3,639,285 | 2/1972 | Nielsen ............................. 252/186 |
| 3,645,911 | 2/1972 | Van Beasuan et al............. 252/186 |
| 3,666,680 | 5/1972 | Briggs ................................. 252/186 |
| 3,847,830 | 11/1974 | Williams et al. .................... 252/186 |

Primary Examiner—Benjamin R. Padgett
Assistant Examiner—Irwin Gluck
Attorney, Agent, or Firm—Larson, Taylor and Hinds

[57] ABSTRACT

Particulate peroxygen compounds such as sodium percarbonate are coated with a copolymer of vinylidene chloride and another copolymerizable monomer. These coated compounds can be used in detergent mixtures. The coating of peroxygen compound with such films protect the compound from the effect of decomposition by wet air during storage while it permits liberation of the peroxygen compound in an aqueous washing solution.

12 Claims, No Drawings

PARTICULATE PEROXYGEN COMPOUNDS

The present invention relates to particulate peroxygen compounds stabilised by coating, to a coating process therefor and to detergent mixtures containing such compounds.

It is well known that peroxygen compounds can be employed as bleaching compounds in powder detergent mixtures. Sodium perborate tetrahydrate is usually employed as a bleaching compound in the standard domestic detergents because it is comparatively stable to decomposition in a detergent medium. However, the practice of using laundry washing and cold steeping techniques is becoming increasingly widespread. Under such conditions, sodium perborate suffers from the disadvantage of dissolving too slowly at 20° C.

It has been suggested that one way of overcoming this disadvantage is to use detergent powders admixed with many other inorganic peroxygen compounds, particularly the percarbonates, perphosphates and peroxy monosulphates of alkali metals, which have suitable dissolution rates. The said peroxygen compounds, particularly the percarbonates, decompose too rapidly, particularly when they are stored in a moist atmosphere. In addition, the other ingredients of the cleaning composition may even trigger decomposition. One method which has been suggested as a way of avoiding this defect involves coating peroxygen compounds with stabilising substances or protective inorganic films, for example a sodium silicate solution (A. Welter — Br. Pat. No. 174891 of 26/7/1920) of certain magnesium salts, for example magnesium sulphate heptahydrate. In this case, comparatively large proportions of coating agents must be used in order to ensure adequate stability and the granules of stored material show a partial tendency to agglomeration.

Another recognised method (H. Guiot — Fr. Pat. No. 893115 of 5/4/1943) involves coating the peroxygen compound particles with a layer of wax, paraffin of a natural or synthetic resin: the amounts of coating agent to be used are smaller in this case, but the coated particles still show a tendency to agglomerate.

According to the present invention there is provided a particulate peroxygen compound comprising a normally unstable alkaline metal persalt coated with a copolymer of vinylidene chloride and another copolymerisable monomer.

In another aspect of the present invention there is provided a process for at least partially stabilising normally unstable alkali metal persalts comprising coating the persalts with a copolymer of vinylidene chloride and another copolymerisable monomer.

Surprisingly, it has been observed that despite the mechanical strength and acknowledged adhesion of such films, the peroxygen compound's coating prepared with such polymers detaches readily in an aqueous washing solution at temperatures below the melting point of these peroxygen compounds. Although coating of peroxygen compound with such films does indeed protect the compounds from the effect of decomposition caused by wet air, it also permits liberation of the peroxygen compound in an aqueous washing solution at ambient temperatures.

The percarbonates, perpyrophosphates, pertripolyphosphates, persilicates and peroxymonosulphates of alkaline metals are among some of the normally unstable peroxygen compounds to which the present invention applies.

Typically, the invention can be applied extremely successfully to stabilisation of sodium percarbonate.

As mentioned above, the coating is a copolymer of vinylidene chloride and another copolymerisable monomer which may be one of the following, for example: vinyl chloride, acrylonitrile or an acrylate, preferably methylacrylate. The copolymer should prreferably contain from 5 to 50 percent by wt. of the other monomer; in the case of the methyl acrylate vinylidene chloride copolymers, the more preferred copolymers are those containing 5 to 15 percent by wt. of methylacrylate.

The persalt should preferably be coated with from 0.5 to 5 percent by wt. An amount of 0.5 percent by wt. is more than enough to ensure that the persalt is at least partially coated and to give increased stability. Generally, there is no point in exceeding an amount of 5 percent for ensuring substantially complete coating.

Use of amounts of coating agent corresponding to 1-2 percent by wt. of the persalt is preferred.

In particular, the peroxygen compound coated in accordance with the invention passes the following test: it loses no more than 15 percent of active oxygen after 4 weeks when admixed in the proportion of 2 percent by wt. of active oxygen with a basic detergent powder, i.e. with a detergent powder containing all the usual ingredients with the exception of any peroxygen compounds, storage being conducted at 28° C and under a relative humidity of 70 percent in sealed cardboard boxes for detergents the internal and external walls of which are coated with a cellulose acetate film. An example of such a base powder is given in Table 2 hereinafter.

Any recognised method can be used for coating the peroxygen compound particles with copolymers and the method is not critical. The copolymer itself can be prepared by any polymerisation technique: in suspension or in emulsion. The use of copolymers obtained by copolymerisation in emulsion is preferred, however.

The copolymer can be used dissolved in an organic solvent. In this case, a solvent with a boiling point below the decomposition temperature of the peroxygen compound must be chosen.

Coating should preferably be done by spraying a copolymer in water emulsion on to constantly moving peroxygen compound particles. Coating can take place in a fluidised bed or a rotary disk, in a rotary drum or in any other similar recognised device. Use of the fluidised bed technique is preferred in view of the fact that it gives a more hermetic, more homogeneous coating than the other methods and all other conditions being equal, results in a saving in coating agent and consequently in water which has to be eliminated by evaporation. The temperature at which coating and evaporation of water is controlled to below the decomposition temperature of the peroxygen compound.

This temperature will vary according to the type of peroxygen compound, but the limit can be set at 100° C. In the case of sodium percarbonate, a comparatively heat sensitive product, it is better not to exceed approx. 80° C.

Certain embodiments of the invention will now be described more fully by way of Example.

EXAMPLE 1

This example contains a description of a discontinuous process for coating preformed granules in a fluidised bed.

The apparatus used consisted of a cylinder of 15 cm diameter and 77 cm height, fitted at the base with a gas distributor plate (2 mm holes) and provided with a pipe bundle for heating with steam maintained at effective pressure of 1 kg/cm².

Initially, 3 kg of homogeneous sodium percarbonate granules of medium diameter 0.400 mm and of free-flowing specific weight 1.15 kg/dm³ were placed in this apparatus.

A stream of air flowing at 33 m³N/h at 120° C was passed through the gas distributor plate and 0.48 kg of an aqueous emulsion of coating agent containing per kg of aqueous emulsion, 125 g of vinylidene chloride/methyl acrylate copolymer containing 93 percent by wt. of vinylidene chloride was introduced via a pneumatic atomiser placed on the wall at a height of 11 cm from the base. On account of the temperature of the air of fluidisation and the heat liberated by the pipe bundle, the temperature of the fluidised bed was maintained at 70° C. The depth of the bed was 30 cm.

After introduction of the aqueous copolymer emulsion, the sodium percarbonate granules, completely coated with vinylidene chloride-methyl acrylate copolymer, were withdrawn from the apparatus.

The median diameter of these granules was 0.410 mm and the free-flowing specific weight was 1.17 kg/dm³.

Initially, the sodium percarbonate had an active oxygen content of 142 g/kg. After coating, the content was still 139 g/kg.

Instead of proceeding discontinuously as above, coating could be conducted continuously in a fluidised bed, when it would be better to use a compartmented bed in order to be able to exercise a certain amount of control over the process. The coated product could be discharged either via a simple overflow device or by elutriation via a pipe located at any level in the bed.

EXAMPLE 2

The process was the same as in Example 1, except that an aqueous emulsion of a vinylidene chloride-methyl acrylate copolymer containing 91% by wt. of vinylidene chloride was employed. Initially, the sodium percarbonate had an active oxygen content of 142 g/kg. After coating, this content was still 139 g/kg.

EXAMPLES 3 to 6

In these Examples sodium percarbonate having the same properties and in the same amount as described in Example 1 was coated by the general method described therein. The specific process conditions used are summarised in Table 1.

Shelf Test

The purpose of the tests described hereafter was to assess the efficiency of the coating of sodium percarbonate granules which were coated in accordance with the invention.

a. Test at 28° C and 70 Percent Relative Humidity

In the "box shelf test" mixtures were tested for stability of the percompound, the mixtures containing 2% of active oxygen comprising 7g of sodium percarbonate (uncoated or coated) or 10.5g of sodium perborate (uncoated; for comparison) and 42g of a commercial detergent powder, having a composition given in Table 2. After homogenisation, the mixtures were placed in cardboard boxes (11.5 × 7.2 cm) coated on both sides with a cellulose acetate film. The boxes thus prepared were then stored at 28° C in an atmosphere of 70 percent relative humidity, some for 2 weeks, others respectively for 4,8 and 12 weeks. After each storage period, the active oxygen content in the powder was determined by direct titration with N/2 KMnO₄ and the active oxygen loss relative to the original active oxygen content was evaluated. The percentage active oxygen loss from coated sodium percarbonate was compared with the percentages corresponding to the active oxygen loss of uncoated sodium percarbonate and sodium perborate (stabler product chosen as a reference) obtained under the same test conditions. The results were expressed in terms of the following formula $$\frac{T_{PCS\ uncoated} - T_{PCS\ coated}}{T_{PCS\ uncoated} - T_{PBS\ uncoated}} \times 100 = x\ \%$$

in which T represented the "active oxygen loss". They showed the percentage improvement in the stability of sodium percarbonate attributable to coating in relation to the stability of uncoated sodium perborate which was taken as a reference because most consumers felt it to be adequate. The active oxygen content was measured by introducing approx. 10g of washing powder weighed to the nearest 0.01g in a 750 cc capacity "Erlenmeyer" flask, adding 100 cc of 6N H₂SO₄, 100 cc of distilled water and 2 drops of silicone anti-foaming agent. The mixture was then shaken until such time as a homogeneous solution was obtained and then titrated with N/2 KMnO₄ until a pink colouration lasting 30 sec. was obtained. A blank test was also performed on an equivalent amount of washing powder not containing persalt. The active oxygen content of the specimen, O, expressed in g of oxygen/kg was given by the relationship $$O,\ g/kg = (a-b) \times \frac{1}{2} \times \frac{1000}{P} \times \frac{0.016}{2}$$

in which
- $a$, cm³, denoted the volume of N/2 KMnO₄ used for titrating the powder containing persalt
- $b$, cm³, denoted the volume of N/2 KMO₄ used for the blank titration
- $p$, g, denoted the weight of sample employed.

The results of the box shelf test performed as described above on sodium percarbonates coated per the Examples 1 and 2, and on uncoated sodium percarbonate and on uncoated sodium perborate are given in Table 3.

These results clearly point to the superiority of the products in accordance with the invention compared with the uncoated sodium percarbonate.

b. Test at 35° C and 70% Relative Humidity

The tests described below were aimed at assessing the effectiveness of the coating in respect to coated sodium percarbonate, coated according to the present invention, under other preservation conditions.

The test involved a box shelf test of mixtures identical to those of the preceding test, containing a commercial washing powder, the composition of which is given in Table 4. After homogenisation, these mixtures were introduced into containers of the same shape as those of the preceding test, but which on this occasion, were made of cardboard lined with micro-crystalline wax, and laminated. These containers were then stored at 35° C in an atmosphere of 80% relative humidity, some for 4 weeks, others for 8 weeks. Subsequent procedure was as described for the previous test.

The results of the box shelf tests which were carried out as above with coated sodium percarbonate in accordance with Examples 1 to 6, as well as with uncoated sodium percarbonate and uncoated sodium perborate, are given in Table 5 below.

These results clearly show the superiority of the invention products over the uncoated sodium percarbonate.

Table 1

|  | Ex. 3 | Ex. 4 | Ex. 5 | Ex. 6 |
|---|---|---|---|---|
| Coating Conditions | | | | |
| Fluidisation air flow m³N/h | 33 | 31 | 29 | 28 |
| Temperature of fluidisation air °C | 110 | 115 | 110 | 120 |
| Coating emulsion introduction time min. | 30 | 30 | 30 | 40 |
| Quantity of coating emulsion Kg | 0.35 | 0.48 | 0.30 | 0.48 |
| Content of copolymer in emulsion g/kg of emulsion | 86 | 125 | 100 | 125 |
| Vinylidene chloride content of copolymer % weight | 93 | 90 | 90 | 87 |
| Nature of Comonomer | methylacrylate | methylacrylate | methylacrylate | methylacrylate |
| Temperature of fluidised bed °C | 70 | 65 | 69 | 68 |
| Properties of coated percarbonate | | | | |
| Average particle size | 0.420 | 0.420 | 0.420 | 0.420 |
| Specific gravity (free flowing) Kg/dm³ | 1.20 | 1.13 | 1.19 | 1.13 |
| Active oxygen content g/Kg | 138.5 | 138 | 138 | 139 |

Table 2

Composition of the commercial powder used for the box shelf test at 28° C and 70 % Relative Humidity

|  | g/100 g |
|---|---|
| Sodium alkyl aryl sulphonate | 24 |
| Phosphates - $Na_5P_3O_{10}$ (x) | 43 |
| Silicates - $Na_2O \cdot 2SiO_2$ (xx) - | 9 |
| $Na_2SO_4$ | 12 |
| $H_2O$ | 12 |

(x) The total weight of phosphates was expressed in terms of $Na_5P_3O_{10}$
(xx) The total weight of silicate was expressed in terms of $Na_2O \cdot 2SiO_2$ In Table 3 the % improvement shown is the % improvement in stability attributable to coating, measured after 12 weeks.

Table 3

| Persalt Coated in Exp. No. | % Active Oxygen Lost After (Weeks) | | | | % improvement |
|---|---|---|---|---|---|
|  | 2 | 4 | 8 | 12 | |
| Uncoated sodium Percarbonate | - | 34 | 50 | 67 | |
| uncoated sodium Perborate | - | 1 | 3 | 4 | |
| Sodium Percarbonate 1 | 2 | 6 | 12 | 16 | 81 |
| Sodium Percarbonate 2 | 8.5 | 14 | 27 | 31 | 57 |

Table 4

Composition of the commercial powder used for the box shelf test at 35° C and 80 % Relative Humidity

|  | g/100 g |
|---|---|
| Sodium alkyl aryl sulphonate | 20 |
| $Na_2CO_3$ | 1 |
| $Na_2O \cdot 2SiO_2$ | 7 |
| $Na_5P_3O_{10}$ | 39 |
| $Na_4P_2O_7$ | 7 |
| $Na_2HPO_4$ | 3 |
| $Na_2SO_4$ | 10 |
| EDTA | 1 |
| $H_2O$ and undetermined constituents | 12 |

Table 5

| Persalt Coated in Exp. No. | % Active Oxygen Lost After (Weeks) | | % improvement |
|---|---|---|---|
|  | 4 | 8 | |
| Uncoated sodium Percarbonate | - | 17 | 25 |
| Uncoated sodium Perborate - | 4 | 6 | |
| Sodium Percarbonate 1 | 0 | 5 | >100 |
| Sodium Percarbonate 2 | 4 | 9 | 84 |
| Sodium Percarbonate 3 | 6 | 13 | 63 |
| Sodium Percarbonate 4 | 5 | 10 | 79 |
| Sodium Percarbonate 5 | 6 | 12 | 68 |
| Sodium Percarbonate 6 | 7 | 14 | 58 |

What we claim is:

1. A stabilized particulate peroxygen compound consisting essentially of particles of a alkali metal persalt coated with a copolymer of vinylidene chloride and another copolymerisable monomer.

2. A process for at least partially stabilising alkali metal persalts comprising coating the persalts with a copolymer of vinylidene chloride and another copolymerisable monomer.

3. A stabilized peroxygen compound as claimed in claim 1 wherein the persalt is an alkali metal percarbonate perpyrophosphate, pertripolyphosphate or peroxymonosulphate.

4. A stabilized peroxygen compound as claimed in claim 3 wherein the persalt is sodium percarbonate.

5. A stabilized compound as claimed in claim 1 wherein the copolymer contains from 5 to 50 percent by weight of the other polymerisable monomer.

6. A stabilized compound as claimed in claim 1 wherein the other polymerisable monomer is an acrylate.

7. A stabilized peroxygen compound as claimed in claim 6 wherein the acrylate is methylacrylate.

8. A stabilized peroxygen compound as claimed in claim 7 wherein the copolymer contains from 5 to 15 percent by weight of methylacrylate.

9. A stabilized peroxygen compound as claimed in claim 1 wherein the coating comprises from 0.5 to 5 percent by weight of the persalt.

10. A stabilized peroxygen compound as claimed in claim 9 wherein the coating comprises from 1 to 2 percent by weight of the persalt.

11. A process as claimed in claim 2 wherein the copolymer is employed in the form of an aqueous emulsion.

12. A process as claimed in claim 2 wherein a bed of the persalt particles is fluidised with an insert gas, and is maintained at a temperature below 100° C.

* * * * *